United States Patent
Kim et al.

(10) Patent No.: US 9,151,745 B2
(45) Date of Patent: Oct. 6, 2015

(54) CHIP FOR INSPECTING TOXICITY AND EFFICACY

(75) Inventors: Sang Jin Kim, Gyunggi-do (KR); Jeong Suong Yang, Gyunggi-do (KR); Bo Sung Ku, Gyunggi-do (KR)

(73) Assignee: Samsung Electro-Mechanics Co., Ltd., Suwon-si (KR)

( * ) Notice: Subject to any disclaimer, the term of this patent is extended or adjusted under 35 U.S.C. 154(b) by 1045 days.

(21) Appl. No.: 12/760,131

(22) Filed: Apr. 14, 2010

(65) Prior Publication Data
US 2011/0207205 A1 Aug. 25, 2011

(30) Foreign Application Priority Data
Feb. 22, 2010 (KR) .................. 10-2010-0015779

(51) Int. Cl.
*C12M 1/34* (2006.01)
*G01N 33/53* (2006.01)
*G01N 33/543* (2006.01)
*B01J 19/00* (2006.01)

(52) U.S. Cl.
CPC ......... *G01N 33/5302* (2013.01); *B01J 19/0046* (2013.01); *G01N 33/54373* (2013.01); *B01J 2219/00722* (2013.01)

(58) Field of Classification Search
CPC .............. G01N 33/5302; G01N 33/54366; G01N 33/54373; B01J 19/0046; B01J 2219/00722; B82Y 30/00

USPC ............ 435/286.3, 305.1; 422/502, 503, 551, 422/553

See application file for complete search history.

(56) References Cited

U.S. PATENT DOCUMENTS 5,002,735 A * 3/1991 Alberhasky et al. ........ 422/82.05
6,277,629 B1 * 8/2001 Wolf et al. ................ 435/288.3

FOREIGN PATENT DOCUMENTS

JP 2001-524329 * 12/2001 ................ B01L 3/00

OTHER PUBLICATIONS

Office Action from counterpart Korean Patent Application No. 10-2010-0015779, mailed May 21, 2012, 4 pages including English summary.

* cited by examiner

*Primary Examiner* — Michael Hobbs
(74) *Attorney, Agent, or Firm* — NSIP Law

(57) ABSTRACT

Disclosed herein is a chip for inspecting toxicity and efficacy, including: a first substrate including fitting holes formed at corners thereof; and a second substrate including gap forming members formed at corners thereof corresponding to the fitting holes to form a gap between the first substrate and the second substrate, and protrusions formed on the gap forming members corresponding to the fitting holes and fitted in the fitting holes. The chip for inspecting toxicity and efficacy is advantageous in that alignment of the chip can be easily performed, in that problems with the emission of fluorescence or the penetration of measuring light in the chip can be solved, and in that the cost of producing the chip can be reduced.

7 Claims, 3 Drawing Sheets

CHIP FOR INSPECTING TOXICITY AND EFFICACY

CROSS REFERENCE TO RELATED APPLICATION

This application claims the benefit of Korean Patent Application No. 10-2010-0015779, filed Feb. 22, 2010, entitled "Chip for Inspecting Toxicity and Efficacy of New Material", which is hereby incorporated by reference in its entirety into this application.

BACKGROUND OF THE INVENTION

1. Technical Field

The present invention relates to a chip for inspecting toxicity and efficacy.

2. Description of the Related Art

Conventionally, for new materials used as the raw materials for new drugs and cosmetics, first, screening work is performed to determine whether or not the new materials have efficacy thereby allowing candidate materials to be selected from among the new materials, following which animal and clinical testing is conducted to analyze the action mechanism and toxicity of the candidate materials in detail.

However, since most candidate materials have toxicity, the above method is disfavored because the candidate materials are poisonous to the human body, causing inefficiency in terms of the period and cost required to develop new drugs or new materials.

Currently, the toxicity of new drugs or new materials is inspected in the early stages of development as part of the effort into preventing the inefficient development of new drugs or new materials.

Generally, the toxicity of candidate materials to cells is inspected by cultivating cells in a well plate and then administering candidate materials into the cultivated cells, the candidate materials having been metabolized by enzymes in the liver.

Meanwhile, the well plate needs a comparatively large amount of reagents and cells. Here, in the case of new materials, there is a problem in that the production cost of new materials is increased due to small quantity multi-product production, and, in the case of cells, there is a problem in that it is difficult to keep the balance of supply and demand.

Therefore, in order to solve the above problems and to maximize the efficiency of screening new materials, currently, technologies for inspecting the toxicity of the new materials by fixing and culturing a very small amount of cells on a solid substrate and then administering a very small amount of drugs into the fixed and cultured cells are being developed.

FIG. 1 is a sectional view showing a conventional chip 100 for inspecting toxicity.

As shown in FIG. 1, the conventional chip 100 for inspecting toxicity includes two glass substrates 110 and 120.

Here, metabolites 112 obtained from the reaction of new materials and enzymes in the liver are disposed on one glass substrate 110, and cells 114 immovably cultured in gel-state droplets are disposed in an array shape on the other glass substrate 120.

This chip 100 for inspecting toxicity includes a gasket 130 for preventing cells from being damaged at the time of attaching the two glass substrates 110 and 120 and for maintaining the gap between the two glass substrates 110 and 120.

In the chip 100 for inspecting toxicity, the lateral and upper sides of the glass substrate 120 are precisely machined so that the glass substrates 110 and 120 can be mechanically aligned at the time of attaching the glass substrates 110 and 120. Also, the gasket 130 is fabricated by patterning a polymer material at the edge of the glass substrate 120 using an ejector and then hardening the patterned polymer material in order to prevent cells from being damaged when the glass substrates 110 and 120 are attached.

In this chip 100 for inspecting toxicity, the attachment of the upper substrate 110 and the lower substrate 120 causes the gap between the upper and lower substrates 110 and 120 to decrease, so that liquid droplets located therebetween overlap each other, with the result that drugs are transferred from the upper glass substrate 110 to the lower glass substrate 120 by the diffusion of the liquid droplets.

In the chip 100 for inspecting toxicity configured such that drugs are transferred from the upper glass substrate 110 to the lower glass substrate 120, the chip 100 is cultured in an environmental chamber for a predetermined period of time, and then the upper glass substrate 110 is removed and the activity of the cells is inspected with a dye or phosphor, thereby finally evaluating the toxicity of candidate materials.

However, the conventional chip 100 for inspecting toxicity is problematic in that the lateral and upper sides of the glass substrate 120, which are used as reference planes at the time of attaching the glass substrates 110 and 120, must be precisely machined in order for the glass substrates 110 and 120 to be mechanically aligned, thus causing inefficiency in terms of the cost of the materials and that of production due to the precise machining of the glass substrate 120.

Further, the conventional chip 100 for inspecting toxicity is problematic because the gasket 130 is disposed between the two glass substrates 110 and 120 in order to prevent the cells from being damaged when the glass substrates 110 and 120 are attached so as to maintain the gap between the two glass substrates 110 and 120, and this gasket 130 is fabricated by patterning a polymer material at the edge of the glass substrate 120 using an ejector and then hardening the patterned polymer material, thus causing deviations in the thickness of the gasket 130.

In this regard, the deviations in thickness of the gasket 130 cause the increase of defective fractions at the time of attaching the glass substrates 110 and 120.

SUMMARY OF THE INVENTION

Accordingly, the present invention has been made to solve the above-mentioned problems, and the present invention provides a chip for inspecting toxicity and efficacy which can prevent the emission of fluorescence or the penetration of measuring light, which can allow upper and lower chips to be easily aligned and separated at the time of attaching the upper and lower chips, and which can reduce the cost of production.

An aspect of the present invention provides a chip for inspecting toxicity and efficacy, including: a first substrate including fitting holes formed at corners thereof; and a second substrate including gap forming members formed at corners thereof corresponding to the fitting holes to form a gap between the first substrate and the second substrate, and protrusions formed on the gap forming members corresponding to the fitting holes and fitted in the fitting holes.

Here, each of the gap forming members may have a diameter larger than that of each of the fitting holes.

Further, each of the protrusions may have a diameter equal to or larger than that of each of the fitting holes.

Further, the gap forming members, the protrusions and the second substrate may be integrally formed by an injection molding process.

Further, the first substrate and the second substrate may be made of plastic.

Further, assuming that the first substrate is divided into two equal half substrates, the fitting holes may be formed at all outer corners of one of both the half substrates whereas the fitting hole may be formed at one outer corner or some outer corners of the other of both the half substrates.

Further, a separating hole may be formed at a central portion of opposite ends of the first substrate.

Further, the separating hole may have a diameter equal to or different from that of the fitting hole.

Further, the center of the separating hole may be positioned at the same level as that of the fitting hole.

The chip for inspecting toxicity and efficacy may further include a separating rod for separating the second substrate from the first substrate by inserting it into the separating hole.

Here, the separating rod may have a diameter equal to or smaller than that of the separating hole.

The terms and words used in the present specification and claims should not be interpreted as being limited to typical meanings or dictionary definitions, but should be interpreted as having meanings and concepts relevant to the technical scope of the present invention based on the rule according to which an inventor can appropriately define the concept of the term to describe the best method he or she knows for carrying out the invention.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
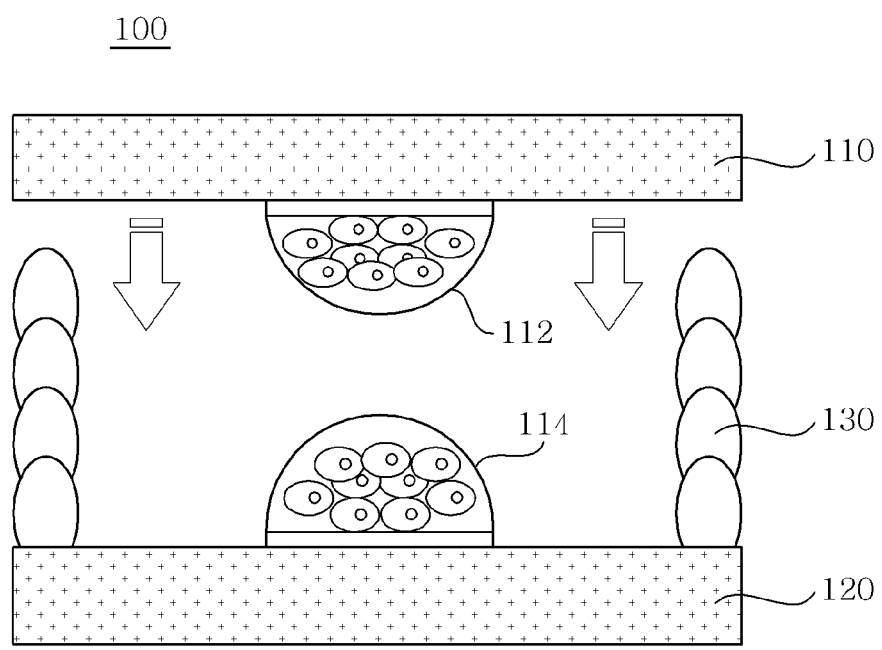
FIG. 1 is a sectional view showing a conventional chip for inspecting toxicity and efficacy.

The objects, features and advantages of the present invention will be more clearly understood from the following detailed description and preferred embodiments taken in conjunction with the accompanying drawings. Throughout the accompanying drawings, the same reference numerals are used to designate the same or similar components, and redundant descriptions thereof are omitted. Further, in the description of the present invention, when it is determined that the detailed description of the related art would obscure the gist of the present invention, the description thereof will be omitted.

Hereinafter, preferred embodiments of the present invention will be described in detail with reference to the attached drawings.

Figure 2:
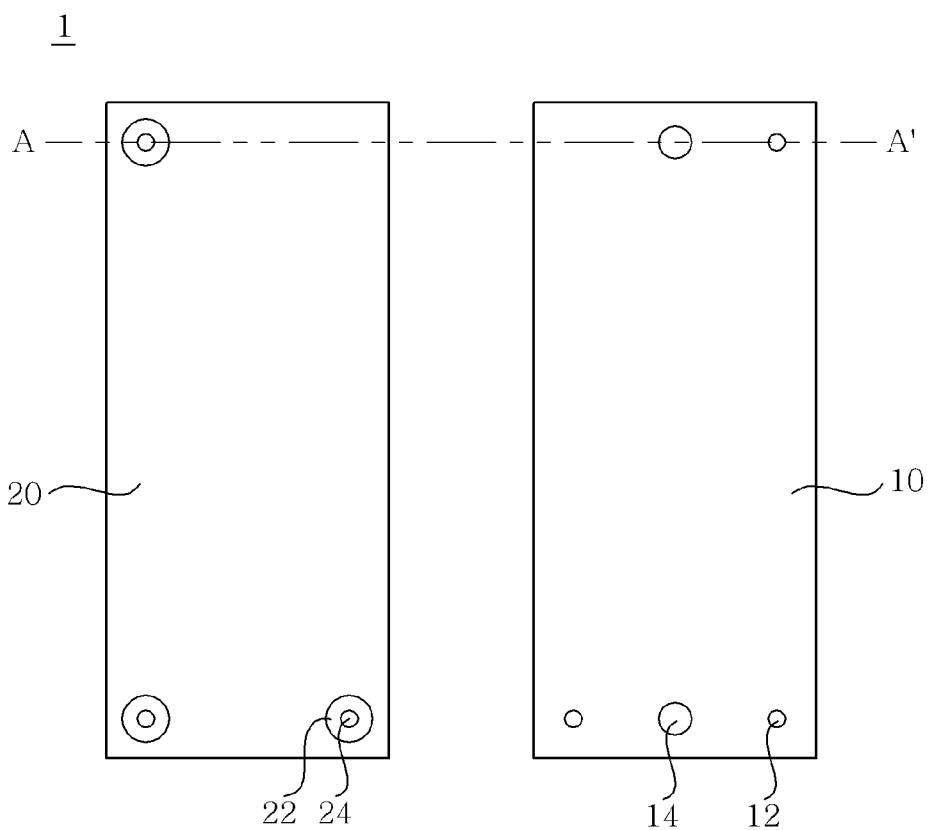
FIG. 2 is a plan view showing a chip for inspecting toxicity and efficacy according to an embodiment of the present invention.
Figure 3:
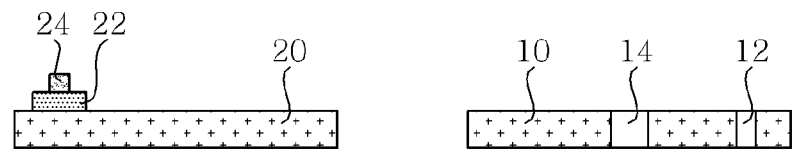
FIG. 3 is a sectional view taken along the line A-A' in FIG. 2 which shows the chip for inspecting toxicity and efficacy.

FIG. 2 is a plan view showing a chip for inspecting toxicity and efficacy according to an embodiment of the present invention, and FIG. 3 is a sectional view taken along the line A-A' in FIG. 2 which shows the chip for inspecting toxicity and efficacy.

As shown in FIGS. 2 and 3, the chip 1 for inspecting toxicity and efficacy according to an embodiment of the present invention includes: a first substrate 10 including fitting holes 12 formed at the corners thereof; and a second substrate 20 including gap forming members 22 formed at the corners thereof corresponding to the fitting holes 12 and forming the gap between the first substrate 10 and the second substrate 20, and protrusions 24 formed on the gap forming members 22 corresponding to the fitting holes 12 and fitted in the fitting holes 12.

In this case, the first substrate 10 and the second substrate 20 are made of plastic, and are fabricated by an injection molding process.

The first substrate 10 includes the fitting holes 12 formed at the corners thereof. The fitting holes 12 may be formed at all corners of the first substrate 10. Alternatively, assuming that the first substrate 10 is divided into upper and lower half substrates by a horizontal center line, the fitting holes may be formed at all outer corners of one of the upper and lower half substrates whereas the fitting hole may be formed at one outer corner or some outer corners of all outer corners of the other of the upper and lower half substrates.

In other words, when the first substrate 10 is formed in a quadrangular shape, the fitting holes 12 may be formed at all of the four corners of the first substrate 10, or, as shown in FIG. 2, may be formed at both two outer corners of the lower half substrate of the first substrate 10 and at any one of the two outer corners of the upper half substrate of the first substrate 10.

Meanwhile, separating holes 14 for separating the second substrate 20 from the first substrate 10 are formed at the central portions of the upper and lower ends of the first substrate 10.

In this case, the separating holes are formed such that their diameters are equal to or different from those of the fitting holes 12, and such that their centers are positioned at the same level as those of the fitting holes 12.

Meanwhile, as shown in FIGS. 2 and 3, the second substrate 20 includes gap forming members 22 formed at the corners thereof corresponding to the fitting holes 12 and forming the gap between the first substrate 10 and the second substrate 20.

In this case, the gap forming members 22 are formed such that their diameters are larger than those of the fitting holes 12 in order to form the gap between the first substrate 10 and the second substrate 20 at the time of attaching the first substrate 10 to the second substrate 20.

The reason why the diameters of the gap forming members 22 are larger than the diameters of the fitting holes 12 is that, if the diameters of the gap forming members 22 are equal to or smaller than the diameters of the fitting holes 12, the gap forming members 22 are inserted into the fitting holes, and thus it is impossible to form a predetermined gap between the first substrate 10 and the second substrate 20.

Meanwhile, protrusions 24 are formed on the gap forming members 22 corresponding to the fitting holes 12 and are fitted in the fitting holes 12.

In this case, the protrusions 24 are formed such that their diameters are equal to or smaller than those of the fitting holes 12, and such that their centers correspond to those of the fitting holes 12.

Thus, when the first substrate 10 and the second substrate 20 are to be attached to each other for the purpose of culturing cells, the protrusions 24 are inserted into the fitting holes 12, thus attaching the first substrate 10 to the second substrate 20.

Meanwhile, the gap forming members 22 and the protrusions 24 may be formed on the second substrate 20 by an injection molding process such that they are integrated with the second substrate 20.

In this chip 1 for inspecting toxicity and efficacy, the fitting holes 12 and the protrusions 24 function to align the first substrate 10 and the second substrate 20 and to attach the first substrate 10 to the second substrate 20, and function as a gasket.

Figure 4:
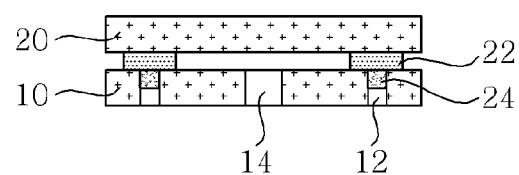
FIG. 4 is a sectional view showing the attached state of the chip for inspecting toxicity and efficacy shown in FIG. 2.
Figure 5:
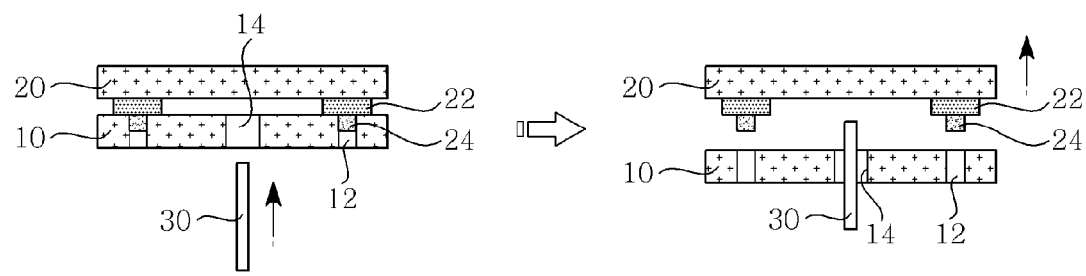
FIG. 5 is a sectional view showing a method of separating the chip for inspecting toxicity and efficacy shown in FIG. 4.

Meanwhile, in the chip 1 for inspecting toxicity and efficacy according to an embodiment of the present invention, metabolized drugs are disposed on one substrate of the first substrate 10 and the second substrate 20, and cells for inspecting toxicity are disposed and fixed in gel state droplets in an array shape on the other substrate thereof to culture the cells in a droplet state, and then, as shown in FIG. 4, the first substrate 10 and the second substrate 20 are attached to each other.

In this case, the first substrate 10 and the second substrate 20 are attached to each other by inserting the protrusions 24 formed on the second substrate 20 into the fitting holes 12 formed in the first substrate 10, thus forming a gap between the first substrate 10 provided with the gap forming members 22 and the second substrate 20.

Subsequently, the chip 1 for inspecting toxicity and efficacy, in which the first substrate 10 and the second substrate 20 are attached to each other, is put into an environmental chamber for a predetermined period of time to culture the cells for inspecting toxicity, and then the first substrate 10 and the second substrate 20 are separated from each other using a separating rod 30.

In this case, the first substrate 10 and the second substrate 20 are separated from each other by inserting the separating rod 30 into the separating hole 14. In order to insert the separating rod 30 into the separating hole 14, the separating rod 30 is formed such that its diameter is equal to or smaller than the diameter of the separating hole 14.

After the first substrate 10 and the second substrate 20 are separated from each other using the separating rod 30, dye or phosphor is administered to the cultured cells, and then the activity of the cells is analyzed, and then the toxicity of the cells is inspected using the analyzed results.

As described above, in the chip 1 for inspecting toxicity and efficacy according to an embodiment of the present invention, the fitting holes 12 are formed in the first substrate 10, and the gap forming members 22 provided thereon with protrusions 24 are formed on the second substrate 20 such that their positions correspond to those of the fitting holes 12, and then the first substrate 10 and the second substrate 20 are attached to each other, thus easily aligning the chip 1 for inspecting toxicity and efficacy.

Further, in the chip 1 for inspecting toxicity and efficacy according to an embodiment of the present invention, the first substrate 10 and the second substrate 20, which are made of plastic, are fabricated by an injection molding process, so that problems with the emission of fluorescence or the penetration of measuring light in the chip 1 for inspecting and efficacy at the time of optical measurement can be solved, and the first substrate 10 and the second substrate 20 don't need to be precisely machined at the time of manufacturing the chip 1 for inspecting toxicity and efficacy, thereby reducing the cost of producing the chip 1 for inspecting toxicity and efficacy.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A chip for inspecting toxicity and efficacy, comprising:
a first substrate including fitting holes formed at corners thereof; and
second substrate including gap forming members formed at corners thereof corresponding to the fitting holes to form a gap between the first substrate and the second substrate by bordering the first and second substrate, and protrusions formed on the gap forming members corresponding to the fitting holes and fitted in the fitting holes;
wherein each of the gap forming members has a diameter larger than that of each of the fitting holes;
wherein each of the protrusions has a diameter equal to or smaller than that of each of the fitting holes;
wherein metabolized drugs for a new material through a reaction with a liver enzyme is disposed in the first substrate and cells cultivated fixedly in gel-state droplets are disposed in the second substrate in an array shape;
a separating hole formed at the upper and lower centers of the first substrate; and,
a separating rod for separating the second substrate from the first substrate by inserting the separating rod into the separating hole, wherein the surface of the separating rod contacting with the second substrate is flat.

2. The chip for inspecting toxicity and efficacy according to claim 1, wherein the gap forming members, the protrusions and the second substrate are integrally, formed by an injection molding process.

3. The chip for inspecting toxicity and efficacy according to claim 1, wherein the first substrate and the second substrate are made of plastic.

4. The chip for inspecting toxicity and efficacy according to claim 1, wherein, when the first substrate is viewed as being divided into two equal half substrates, the fitting holes are formed at all outer corners of one of both the half substrates whereas the fitting hole is formed at one outer corner or some outer corners of the other of both the half substrates.

5. The chip for inspecting toxicity and efficacy according to claim 1, wherein the separating hole has a diameter equal to or different from that of the fitting hole.

6. The chip for inspecting toxicity and efficacy according to claim 1, wherein a center of the separating hole is positioned at the same level as that of the fitting hole.

7. The chip for inspecting toxicity and efficacy according to claim 1, wherein the separating rod has a diameter equal to or smaller than that of the separating hole.

* * * * *